United States Patent
Wakamori et al.

(10) Patent No.: US 7,531,691 B2
(45) Date of Patent: May 12, 2009

(54) METHOD FOR PRODUCING NAPHTHALENE CARBOXYLIC ACID AMIDE COMPOUND

(75) Inventors: Hiroyuki Wakamori, Osaka (JP); Nobuhiro Yonetani, Osaka (JP)

(73) Assignee: Ueno Fine Chemicals Industry, Ltd., Osaka-fu (JP)

( * ) Notice: Subject to any disclaimer, the term of this patent is extended or adjusted under 35 U.S.C. 154(b) by 142 days.

(21) Appl. No.: 11/808,503

(22) Filed: Jun. 11, 2007

(65) Prior Publication Data
US 2008/0045720 A1 Feb. 21, 2008

(30) Foreign Application Priority Data
Jun. 16, 2006 (JP) ............................. 2006-167463

(51) Int. Cl.
*C07C 231/00* (2006.01)
(52) U.S. Cl. ..................................... 564/142
(58) Field of Classification Search ........................ None
See application file for complete search history.

(56) References Cited

U.S. PATENT DOCUMENTS
2005/0182091 A1   8/2005   Brown et al.

FOREIGN PATENT DOCUMENTS
| EP | 1 652 837 A1 | 3/2006 |
| JP | 62-120348 | 6/1987 |
| JP | 63-174963 A | 7/1988 |
| WO | 96/32366 | 10/1996 |
| WO | 00/23525 | 4/2000 |
| WO | 01/87859 | 11/2001 |
| WO | 2005/012231 A1 | 2/2007 |

OTHER PUBLICATIONS

Finan et al., "The Preparation of Acid amides from acid chlorides," Journal of the Chemical Society, 1962, pp. 2824-2825.
Hall et al., "Cytosporone E; racemic synthesis and preliminary antibacterial testing," Bioorganic & Medicinal Chemistry, Elsevier Science, Ltd, GB, Feb. 15, 2005, vol. 13,No. 4,pp. 1409-1413.

*Primary Examiner*—Fiona T Powers
(74) *Attorney, Agent, or Firm*—Sughrue Mion, PLLC

(57) ABSTRACT

The present invention provides a method for producing a naphthalenecarboxylic acid amide compound represented by formula [1] comprising, reacting a naphthalenecarboxylic acid halide compound represented by formula [2] with ammonium acetate in a solvent having an ether bond.

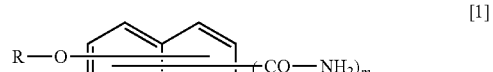

[1]

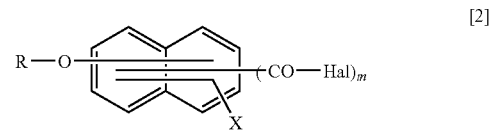

[2]

According to the method of the present invention, a naphthalene carboxylic acid amide compound can be obtained at high yield and at low cost.

8 Claims, No Drawings

METHOD FOR PRODUCING NAPHTHALENE CARBOXYLIC ACID AMIDE COMPOUND

TECHNICAL FIELD

The present invention relates to a method for producing a naphthalene carboxylic acid amide compound.

BACKGROUND OF THE INVENTION

Hydroxynaphthalenecarboxylic acid amide compounds are important compounds used for synthesizing a wide variety of materials, for example, organic dyes such as azo dyes, medical and agricultural chemicals. Such compounds are derived from hydroxynaphthalenecarboxylic acid compounds such as 2-hydroxy-6-naphthoic acid, 2-hydroxy-3-naphthoic acid and 2-hydroxynaphthalene-3,6-dicarboxylic acid.

A conventionally used method for producing a hydroxynaphthalenecarboxylic acid amide compound comprises amidating an acid halide of a hydroxynaphthalenecarboxylic acid compound with an amidating reagent such as ammonia gas and aqueous ammonia (see WO2005/012231, Japanese Patent Application Laid Open (Kokai) Nos. S62-120348 and S63-174963).

However, ammonia gas or aqueous ammonia may cause mucosal irritation and may develop rancid odor. Therefore, said method is not preferable in terms of the working environment. Further, ammonia gas has difficulties in handlings, such as controlling the gas flow rate, due to its gaseous properties. Furthermore, when the amidation step is performed by introducing ammonia gas into the reaction mixture, a hydroxynaphthoic acid amide compound, which is the reaction product, tends to be precipitated near the end of the gas introducing tube, which may result in the pipe blockage.

Another amidation method known to the art comprises amidating a hydroxynaphthalenecarboxylic acid compound with ammonium carbonate in the presence of 1-(3-dimethylaminopropyl)-3-ethylcarbodiimide hydrochloride and 1-hydroxybenzothiazole using N,N-dimethylformamide as a solvent (see US-A-2005/0182091, Preparation 58).

However, the method disclosed in US-A-2005/0182091 is not industrially advantageous because it uses a large amount of expensive reagents such as 1-(3-dimethylaminopropyl)-3-ethylcarbodiimide hydrochloride and 1-hydroxybenzothiazole.

Accordingly, there is a demand for a method for producing a hydroxynaphthalenecarboxylic acid amide compound using an inexpensive amidating reagent which is less harmful to the working environment.

SUMMARY OF THE INVENTION

An object of the present invention is to provide a method for producing a naphthalenecarboxylic acid amide compound which uses an inexpensive and less harmful amidating reagent and can provide the product in an yield equal to or better than conventional methods which use gaseous or aqueous ammonia.

The present invention provides a method for producing a naphthalenecarboxylic acid amide compound represented by formula [1] comprising, reacting a naphthalenecarboxylic acid halide compound represented by formula [2] with ammonium acetate in a solvent having an ether bond:

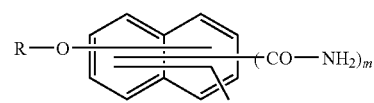

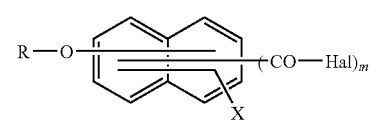

wherein, Hal is chlorine or bromine;

m is an integer of 1 or 2;

R is selected from the group consisting of hydrogen, an optionally branched saturated alkyl having 1-20 carbon atoms, an aralkyl having 7-12 carbon atoms, an optionally branched saturated alkanoyl having 2-20 carbon atoms and benzoyl group;

X is selected from the group consisting of hydrogen, cyano, a group represented by formulae [3], [4] and [5]:

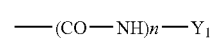

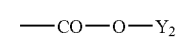

provided that when m is 2, X is hydrogen;

n is an integer of 1 or 2;

$Y_1$ is selected from the group consisting of hydrogen, an optionally branched and optionally unsaturated aliphatic group having 1-20 carbon atoms, an optionally substituted aromatic group and an optionally substituted heterocyclic group having conjugated double bonds;

$Y_2$ is an optionally branched and optionally unsaturated aliphatic group having 1-20 carbon atoms;

Z is —O—, —S— or —NH—; and

A is selected from the group consisting of an optionally substituted aromatic group and an optionally substituted heterocyclic group having conjugated double bonds.

In the specification and claims, the term "aromatic group" represents a 6-membered monocyclic group or a condensed ring group consisting of up to 4 aromatic rings.

"Heterocyclic group having conjugated double bonds" represents a 5- or 6-membered monocyclic group or a condensed ring group having at least one hetero atom selected from N, S and O and conjugated double bonds. When it constitutes a condensed ring group, said group may have up to 6 rings.

In the method of the present invention, a naphthalenecarboxylic acid halide compound represented by formula [2] which is used as a starting material can be produced by any methods known to the art.

For example, a naphthalenecarboxylic acid halide compound can be prepared by the method comprising reacting a naphthalenecarboxylic acid compound represented by formula [9] with an acid halogenating agent such as thionyl chloride, thionyl bromide and oxalyl chloride in a solvent such as toluene, xylene and tetrahydrofuran to give an acid halide compound and removing the solvent and the excess acid halogenating agent under atmospheric pressure or reduced pressure:

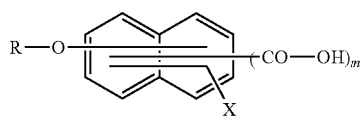

[9]

wherein, m, R and X are the same as defined above.

The temperature of the reaction of a naphthalenecarboxylic acid compound represented by formula [9] with an acid halogenating agent is preferably 0-80° C., and more preferably 30-50° C. Examples of the solvent used for the reaction include tetrahydrofuran, toluene and xylene. The reaction may be conducted in air, but the reaction may preferably be conducted under inert gas atmosphere, for example, under nitrogen or helium gas atmosphere. The reaction pressure is not limited and may be atmospheric pressure, increased pressure and reduced pressure. The reaction time may vary depending on the type of the selected naphthalenecarboxylic acid compound, and is generally 0.5-20 hours, and preferably 0.5-5 hours.

Examples of the preferable naphthalenecarboxylic acid compounds represented by formula [9] used as starting materials for producing naphthalenecarboxylic acid halide compounds represented by formula [2] include, 1-hydroxy-2-naphthoic acid, 1-hydroxy-4-naphthoic acid, 1-hydroxy-6-naphthoic acid, 2-hydroxy-1-naphthoic acid, 2-hydroxy-4-naphthoic acid, 2-hydroxy-5-naphthoic acid, 2-hydroxy-7-naphthoic acid, 2-hydroxy-8-naphthoic acid, 2-hydroxynaphthalene-1,6-dicarboxylic acid and derivatives which are obtained by substituting hydroxy group of the above-listed naphthalenecarboxylic acid compounds with methyl, benzyl or acetyl group as well as compounds represented by following formulae [I], [II] and [III]:

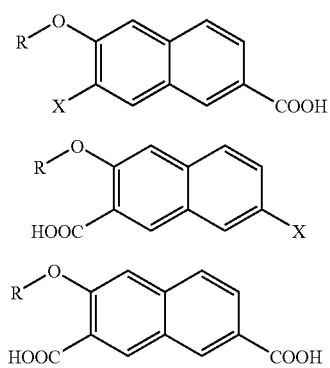

wherein, R and X are the same as defined above.

Among these naphthalenecarboxylic acid compounds, compounds represented by formulae [I], [II] and [III] are especially preferable.

Examples of compounds represented by formulae [I], [II] and [III] include 2-hydroxy-3-naphthoic acid, 2-acetoxy-3-naphthoic acid, 2-hydroxy-6-naphthoic acid, 2-acetoxy-6-naphthoic acid, 2-hydroxynaphthalene-3,6-dicarboxylic acid, 2-acetoxynaphthalene-3,6-dicarboxylic acid, 2-hydroxy-3-methoxycarbonyl-6-naphthalenecarboxylic acid, 2-hydroxy-3-ethoxycarbonyl-6-naphthalenecarboxylic acid, 2-hydroxy-3-n-butoxycarbonyl-6-naphthalenecarboxylic acid, 2-hydroxy-3-phenylaminocarbonyl-6-naphthalenecarboxylic acid, 2-hydroxy-6-methoxycarbonyl-3-naphthalenecarboxylic acid, 2-hydroxy-6-ethoxycarbonyl-3-naphthalenecarboxylic acid, 2-hydroxy-6-n-butoxycarbonyl-3-naphthalenecarboxylic acid and 2-hydroxy-6-phenylaminocarbonyl-3-naphthalenecarboxylic acid.

The most preferable compounds among the compounds represented by formulae [I], [II] and [III] are 2-hydroxy-3-naphthoic acid, 2-hydroxy-6-naphthoic acid, 2-hydroxynaphthalene-3,6-dicarboxylic acid, 2-acetoxy-3-naphthoic acid, 2-acetoxy-6-naphthoic acid and 2-acetoxy-naphthalene-3,6-dicarboxylic acid.

Methods for producing these naphthalenecarboxylic acid compounds represented by formula [9] are not limited and any known methods may be employed. For example, Kolbe-Schmitt reaction which comprises reacting an alkaline metal of naphthol with carbon dioxide may be employed. Naphthalenecarboxylic acid compounds represented by formula [9] may also be produced by a method comprising oxidizing a naphthol compound having alkyl, acyl or formyl group and having alkyl-, aralkyl- or acyl-protected hydroxy group with free oxygen in the presence of a catalyst containing metal such as cobalt and manganese and, if desired, deprotecting the protected-hydroxy group.

In the naphthalenecarboxylic acid halide compound represented by formula [2], R is selected from the group consisting of hydrogen, an optionally branched saturated alkyl having 1-20 carbon atoms, an aralkyl having 7-12 carbon atoms, an optionally branched saturated alkanoyl having 2-20 carbon atoms and benzoyl group.

When R is an optionally branched saturated alkyl having 1-20 carbon atoms, examples of R include methyl, ethyl, n-propyl, isopropyl, isobutyl, sec-butyl, tert-butyl, n-butyl, isopentyl, neopentyl, tert-pentyl, n-pentyl, isohexyl, n-hexyl, n-octyl, n-nonyl, n-decyl, n-dodecyl, n-hexadecyl and n-octadecyl groups.

When R is an aralkyl having 7-12 carbon atoms, examples of R include benzyl, phenethyl, 1-naphthylmethyl and 2-naphthylmethyl.

When R is an optionally branched saturated alkanoyl having 2-20 carbon atoms, examples of R include acetyl, propionyl, 2-methylpropanoyl, butanoyl, 3-methylbutanoyl, 2,2-dimethylpropanoyl, pentanoyl, 3-methylbutanoyl, hexanoyl, octanoyl, decanoyl, lauroyl, myristoyl, palmitoyl and stearoyl groups.

In formula [2], X is selected from the group consisting of hydrogen, cyano and groups represented by formulae [3], [4] and [5].

When X is a group represented by formula [3], examples of X include alkylaminocarbonyl, naphthylaminocarbonyl, phenylaminocarbonyl and aminocarbonyl groups.

In formula [3], $Y_1$ is selected from the group consisting of hydrogen, an optionally branched and optionally unsaturated aliphatic group having 1-20 carbon atoms, an optionally substituted aromatic group and an optionally substituted heterocyclic group having conjugated double bonds.

When $Y_1$ is an optionally branched and optionally unsaturated aliphatic group having 1-20 carbon atoms, examples of $Y_1$ include methyl, ethyl, n-propyl, isopropyl, isobutyl, sec-butyl, tert-butyl, n-butyl, isopentyl, neopentyl, tert-pentyl, n-pentyl, isohexyl, n-hexyl, n-octyl, n-nonyl, n-decyl, n-dodecyl, n-hexadecyl, n-octadecyl, vinyl and allyl groups.

When $Y_1$ is an optionally substituted aromatic group, examples of $Y_1$ include phenyl, naphthyl and anthraquinonyl groups.

When $Y_1$ is an optionally substituted heterocyclic group having conjugated double bonds, examples of heterocycle groups constituting the heterocyclic groups include thiophene, furan, pyrrole, imidazole, pyrazole, isothiazole, isoxazole, pyridine, pyrazine, pyrimidine, pyridazine, triazole, tetrazole, indole, 1H-indazole, purine, 4H-quinolizine, isoquinoline, quinoline, phthalazine, naphthyridine, quinoxaline, quinazoline, cinnoline, pteridine, benzofuran, benzoxazole, benzothiazole, benzimidazole, benzimidazolone and phthalimide.

When $Y_1$ is an aromatic group or a heterocyclic group having conjugated double bonds, examples of substituents that $Y_1$ may have include, halogen, halogenated alkyl having 1-6 carbon atoms, nitro, alkyl having 1-6 carbon atoms, alkoxy having 1-6 carbon atoms, cyano, phenoxy, amino, alkanoylamino having 2-6 carbon atoms, benzoylamino, hydroxy, alkoxycarboxyl having 2-6 carbon atoms, phenoxycarbonyl, alkylaminocarbonyl having 2-6 carbon atoms, phenylaminocarbonyl, alkylaminosulfonyl having 1-6 carbon atoms and alkenyl having 2-6 carbon atoms. When $Y_1$ has two or more substituents, they may be the same or different.

When the substituent on $Y_1$ contains aromatic group(s), the aromatic group may have one or more further substituents which are selected from the group consisting of halogen, alkyl having 1-6 carbon atoms, alkoxy having 1-6 carbon atoms and cyano group.

When $Y_1$ is an aromatic group or a heterocyclic group having conjugated double bonds, examples of substituents on the aromatic group or the heterocyclic group include halogen such as chloro, bromo, iodo and fluoro; halogenated alkyl having 1-6 carbon atoms such as chloromethyl, 2-chloroethyl, 3-chloroethyl and trifluoromethyl; nitro; alkyl having 1-6 carbon atoms such as methyl, ethyl, n-propyl, isopropyl, isobutyl, sec-butyl, tert-butyl, n-butyl, isopentyl, neopentyl, tert-pentyl, n-pentyl, isohexyl and n-hexyl; alkoxy having 1-6 carbon atoms such as methoxy, ethoxy, n-propyloxy, n-butoxy and n-hexyloxy; cyano; phenoxy; amino; alkanoylamino having 2-6 carbon atoms such as acetylamino, propionylamino, butanoylamino and pentanoylamino; benzoylamino; hydroxy; alkoxycarboxyl having 2-6 carbon atoms such as methoxycarbonyl, ethoxycarbonyl, n-propyloxycarbonyl, n-butoxycarbonyl and n-hexyloxycarbonyl; phenoxycarbonyl; alkylaminocarbonyl having 2-6 carbon atoms such as methylaminocarbonyl, ethylaminocarbonyl, n-propylaminocarbonyl, n-butylaminocarbonyl and hexylaminocarbonyl; phenylaminocarbonyl; alkylaminosulfonyl having 1-6 carbon atoms such as methylaminosulfonyl, ethylaminosulfonyl, n-propylaminosulfonyl, n-butylaminosulfonyl, n-propylaminosulfonyl and n-hexylaminosulfonyl; and alkenyl having 2-6 carbon atoms such as vinyl and allyl.

When X in the naphthalenecarboxylic acid halide compound represented by formula [2] is a group represented by formula [4], $Y_2$ is an optionally branched and optionally unsaturated aliphatic group having 1-20 carbon atoms. Examples of such $Y_2$ include methyl, ethyl, n-propyl, isopropyl, n-butyl, isobutyl, tert-butyl, n-pentyl, n-octyl, n-nonyl, n-decyl, n-dodecyl, n-hexadecyl, n-octadecyl, vinyl and allyl.

When X in the naphthalenecarboxylic acid halide compound represented by formula [2] is a group represented by formula [5], Z is —O—, —S— or —NH—, and A is selected from the group consisting of an optionally substituted aromatic group and an optionally substituted heterocyclic group having conjugated double bonds.

When A is an optionally substituted aromatic group, examples of A include aromatic groups such as benzene, naphthalene and anthraquinone.

When A is an optionally substituted heterocyclic group having conjugated double bonds, examples of A include thiophene, furan, pyrrole, imidazole, pyrazole, isothiazole, isoxazole, pyridine, pyrazine, pyrimidine, pyridazine, triazole, tetrazole, indole, 1H-indazole, purine, 4H-quinolizine, isoquinoline, quinoline, phthalazine, naphthyridine, quinoxaline, quinazoline, cinnoline, pteridine, benzofuran, benzoxazole, benzothiazole, benzimidazole, benzimidazolone and phthalimide.

When A is an aromatic group or a heterocyclic group having conjugated double bonds, examples of substituents that A may have are the same as those which $Y_1$ may have.

When X in the naphthalenecarboxylic acid halide compound represented by formula [2] is other than hydrogen, the naphthalenecarboxylic acid halide compound may be produced by referring to the methods disclosed in WO96/032366, WO00/023525, WO01/087859 and WO2005/012231 and the like.

In the naphthalenecarboxylic acid halide compound represented by formula [2], halogen (Hal) constituting the halogenocarbonyl group is chlorine or bromine. Among these halogen atoms, chlorine is preferable in terms of the ease in preparing the naphthalenecarboxylic acid halide compound and the reactivity upon amidation reaction.

Examples of preferable naphthalenecarboxylic acid halide compounds represented by formula [2] include 1-hydroxy-2-naphthoic acid chloride, 1-hydroxy-4-naphthoic acid chloride, 1-hydroxy-6-naphthoic acid chloride, 2-hydroxyl-naphthoic acid chloride, 2-hydroxy-4-naphthoic acid chloride, 2-hydroxy-5-naphthoic acid chloride, 2-hydroxy-7-naphthoic acid chloride, 2-hydroxy-8-naphthoic acid chloride, 2-hydroxynaphthalene-1,6-dicarboxylic acid dichloride, derivatives thereof whose hydroxy groups are modified with methyl, benzyl or acetyl groups as well as compounds represented by following formulae [6], [7] and [8]:

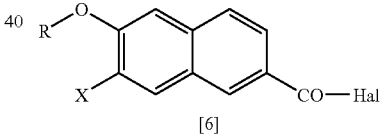

[6]

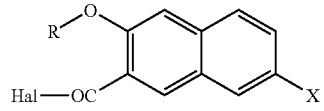

[7]

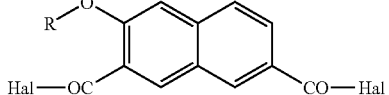

[8]

wherein, R and X are the same as defined above.

Among the above-listed naphthalenecarboxylic acid halide compounds, compounds represented by formulae [6], [7] and [8] are especially preferable. Examples of compounds represented by formulae [6], [7] and [8] include 2-hydroxy-3-naphthoic acid chloride, 2-acetoxy-3-naphthoic acid chloride, 2-hydroxy-6-naphthoic acid chloride, 2-acetoxy-6-naphthoic acid chloride, 2-hydroxynaphthalene-3,6-dicarboxylic acid dichloride, 2-acetoxynaphthalene-3,6-dicarboxylic acid dichloride, 2-hydroxy-3-methoxycarbonyl-6-naphthalenecarboxylic acid chloride, 2-hydroxy-3-ethoxycarbonyl-6-naphthalenecarboxylic acid chloride, 2-hydroxy-3-n-butoxycarbonyl-6-naphthalenecarboxylic acid chloride, 2-hydroxy-3-phenylaminocarbonyl-6-naphthalenecarboxylic acid chloride, 2-hydroxy-6-methoxycarbonyl-3-naphthalenecarboxylic acid chloride, 2-hydroxy-6-ethoxycarbonyl-3-naphthalenecarboxylic acid chloride, 2-hydroxy-6-n-butoxycarbonyl-3-naphthalenecarboxylic acid chloride and 2-hydroxy-6-phenylaminocarbonyl-3-naphthalenecarboxylic acid chloride.

Among the compounds represented by formulae [6], [7] and [8], the most preferable compounds are 2-hydroxy-3-naphthoic acid chloride, 2-hydroxy-6-naphthoic acid chloride, 2-hydroxynaphthalene-3,6-dicarboxylic acid dichloride, 2-acetoxy-3-naphthoic acid chloride, 2-acetoxy-6-naphthoic acid chloride and 2-acetoxynaphthalene-3,6-dicarboxylic acid dichloride.

In the method of the present invention, the naphthalenecarboxylic acid halide compound represented by formula [2] is subjected to the reaction with ammonium acetate to yield the naphthalenecarboxylic acid amide compound represented by formula [1].

In the method of the present invention, ammonium acetate may be in the form of powder, or provided as a suspension or solution in a solvent having an ether bond.

The amount of ammonium acetate used in the amidation reaction is preferably 0.8-10 moles, more preferably 1.0-7 moles and most preferably 1.2-5 moles per 1 mole of halogenocarbonyl group in a naphthalenecarboxylic acid halide compound represented by formula [2].

Ammonium acetate used for the present invention may preferably be a high-purity compound, but may be a crude compound containing other ammonium salts than acetate such as ammonium formate, ammonium propionate, ammonium carbonate, ammonium sulfate, ammonium chloride and ammonium nitrate.

When crude ammonium acetate contains other ammonium salts, the amount of ammonium acetate may be preferably not less than 80 parts by weight, more preferably not less than 90 parts by weight, especially preferably not less than 95 parts by weight per 100 parts by weight of the total weight of ammonium acetate and other ammonium salts.

When crude ammonium acetate containing other ammonium salts is used for the reaction, the amount of the crude compound may be determined by considering the purity of ammonium acetate in the crude compound.

In the method of the present invention, the reaction of the naphthalenecarboxylic acid halide compound represented by formula [2] with ammonium acetate is carried out in a solvent having an ether bond. The molecular structure of the solvent used for the present invention may be straight, branched or cyclic structure. The solvent having an ether bond used for the present invention is not limited as long as it exists as liquid under the condition of the reaction. When the reaction temperature exceeds the boiling point of the solvent under atmospheric pressure, the reaction may be carried out in a pressure-resistant container.

Preferable solvents used for the present invention are those which exist as liquids at temperatures between −40° C. and 100° C. under atmospheric pressure.

Examples of solvents preferably used for the present invention include tetrahydrofuran, 1,4-dioxane, trioxane, furan, 2-methylfuran, dimethylether, diethylether, di-n-propylether, diisopropylether, di-n-butylether, anisole, phenetol, o-methoxytoluene, m-methoxytoluene, p-methoxytoluene, ethylene glycol dimethylether, ethylene glycol diethylether, ethylene glycol dibutylether, diethylene glycol dimethylether, diethylene glycol diethylether, diethylene glycol dibutylether and mixture thereof.

Among the above solvents, tetrahydrofuran without other solvents is especially preferable. By using tetrahydrofuran, the reaction proceeds well, the product can be easily collected and the solvent can be recycled by purifying the same after the reaction.

In the method of the present invention, a solvent which does not have an ether bond can be used with a solvent having an ether bond.

Examples of solvents having no ether bond which can be used for the method of the present invention include; aromatic solvents such as benzene, toluene, xylene, mesitylene, chlorobenzene, dichlorobenzene and nitrobenzene; aliphatic ethers such as ethyl acetate and butyl acetate; aliphatic hydrocarbons such as hexane and octane; halogenated hydrocarbons such as methylene chloride, trichloromethane, tetrachloromethane and 1,2-dichloroethane; ketones such as acetone, methylethylketone, methylisobutylketone, cyclohexanone and acetophenone; nitrogen-containing solvents such as acetonitrile, propionitrile, pyridine, N,N-dimethylformamide, N,N-dimethylacetamide and N-methyl-2-pyrrolidone.

In the method of the present invention, when a solvent having no ether bond is used together with a solvent having an ether bond, the amount of the solvent having no ether bond is not more than 50 parts by weight, preferably not more than 30 parts by weight and more preferably not more than 10 parts by weight per 100 parts by weight of the total amount of the solvents.

In the method of the present invention, the reaction of a naphthalenecarboxylic acid halide compound represented by formula [2] with ammonium acetate may be carried out batchwisely or continuously.

Exemplary embodiments of the reaction of a naphthalenecarboxylic acid halide compound represented by formula [2] with ammonium acetate in a solvent having an ether bond include:

1) a process which comprises:

preparing a mixture of a solvent having an ether bond and a naphthalenecarboxylic acid halide compound represented by formula [2] in a reaction container, feeding ammonium acetate in the form of powder or as a mixture with the solvent into the reaction container, and stirring the resulting reaction mixture;

2) a process which comprises:

preparing a mixture of a solvent having an ether bond and ammonium acetate in a reaction container, feeding a naphthalenecarboxylic acid halide compound represented by formula [2] in the form of solid or as a mixture with the solvent into the reaction container, and stirring the resulting reaction mixture;

3) a process which comprises:

preparing a mixture of a solvent having an ether bond and a naphthalenecarboxylic acid halide compound represented by formula [2] as well as a mixture of ammonium acetate and a solvent having an ether bond, feeding these mixtures into a reaction container simultaneously, and stirring the resulting reaction mixture; and, 4) a process which comprises:

feeding a solvent having an ether bond into a reaction container, adding a naphthalenecarboxylic acid halide compound in the form of solid and ammonium acetate in the form of powder simultaneously to the solvent, and stirring the resulting reaction mixture.

Among the above embodiments 1) to 4), the embodiment 2) is preferable because of the high reaction yield and the less formation of side-product.

In the embodiment 2), the mixture of the solvent having an ether bond and ammonium acetate is preferably kept as it is for from 10 minutes to 5 hours, more preferably for from 15 minutes to 4 hours, even more preferably for from 30 minutes to 3 hours before adding the naphthalenecarboxylic acid halide compound represented by formula [2] to the mixture in terms of the reaction yield.

In the embodiments 1) to 4), the manner of the feeding the naphthalenecarboxylic acid halide compound represented by formula [2] and/or ammonium acetate into the reaction container is not limited. The reactants may be fed at one time or by portions continuously or intermittently. However, the reactants may preferably be fed by portions continuously or intermittently in terms of less formation of side-product.

The reaction container used for the reaction is not limited and any known reaction containers can be used as long as the reaction mixture in the container can be stirred sufficiently.

The reaction pressure is not limited. The reaction may be done under reduced pressure, increased pressure or atmospheric pressure. The reaction may be carried out in air, but the reaction is preferably carried out under inert gas atmosphere such as nitrogen, neon and argon gas atmosphere. The reaction temperature is not limited as long as the reaction proceeds well. The temperature may be determined depending on the selected naphthalenecarboxylic acid halide compound as well as the type and amount of the selected solvent.

The amidation reaction of a naphthalenecarboxylic acid halide compound represented by formula [2] with ammonium acetate is carried out preferably at a temperature of $-40$-$100°$ C. and more preferably at a temperature of $-20$-$80°$ C. and the most preferably at a temperature of $0$-$60°$ C.

The reaction time may vary depending on the reaction temperature and the types of the naphthalenecarboxylic acid halide compound and the solvent, but may preferably be 15 minutes to 10 hours.

The resulting naphthalenecarboxylic acid amide compound represented by formula [1] obtained by employing the above-described reaction conditions is then collected. If the naphthalenecarboxylic acid amide compound is precipitated from the reaction mixture, the compound may be collected by conventional methods such as centrifugation and filter press. If the compound is dissolved in the reaction solution, the solution may be concentrated so as to precipitate the naphthalenecarboxylic acid amide compound and then the compound may be collected by the conventional methods.

If necessary, the collected naphthalenecarboxylic acid amide compound represented by formula [1] is washed with water, methanol or aqueous methanol, purified by recrystallization using an appropriate solvent. The resulting naphthalenecarboxylic acid amide compound represented by formula [1] is suitably used as a starting material for various products, for example, organic dyes such as azo dyes, medical and agricultural chemicals and the like.

The present invention is further described in reference to the following examples. The examples are intended to illustrate the invention and are not to be construed to limit the scope of the invention.

EXAMPLES

Example 1

[Acid Chlorination Reaction]

23.1 g (0.1 mole) of 2-acetoxy-6-naphthoic acid, 0.1 g of N,N-dimethylformamide and 185 g of tetrahydrofuran were fed into. 300 ml-glass container. To this mixture, 23.9 g of thionyl chloride was added dropwise at room temperature under stirring. Then, the reaction was heated to 50° C. and kept at this temperature for 30 minutes. From the resulting mixture, tetrahydrofuran and the excess thionyl chloride were distilled out using a rotary evaporator to give 24.9 g (0.1 mole) of 2-acetoxy-6-naphthoic acid chloride.

[Amidation Reaction]

15.4 g (0.2 mole) of ammonium acetate and 69.3 g of tetrahydrofuran were fed in 300 ml-glass container and the mixture was kept at 20° C. for one hour under stirring.

Then, 2-acetoxy-6-naphthoic acid chloride obtained by the acid chlorination reaction was dissolved in 115.5 g of tetrahydrofuran. The resulting mixture was added dropwise to the suspension of ammonium acetate in tetrahydrofuran over 15 minutes. The mixture was kept at 20° C. for 30 minutes.

Thereafter, the resulting reaction mixture was subjected to high performance liquid chromatography (HPLC). The yield of 2-acetoxy-6-naphthoic acid amide to the starting material, 2-acetoxy-6-naphthoic acid chloride, was found to be 94 mole %.

Example 2

[Acid Chlorination Reaction]

The acid chlorination reaction was carried out in the same manner as Example 1 except that 18.8 g (0.1 mole) of 2-hydroxy-3-naphthoic acid was used instead of 23.1 g (0.1 mole) of 2-acetoxy-6-naphthoic acid and 94 g of tetrahydrofuran was used. 20.6 g (0.1 mole) of 2-hydroxy-3-naphthoic acid chloride was obtained.

[Amidation Reaction]

The amidation reaction was carried out in the same manner as Example 1 except that 2-hydroxy-3-naphthoic acid chloride obtained by the acid chlorination reaction was dissolved in 25 g of tetrahydrofuran.

The resulting reaction mixture was subjected to high performance liquid chromatography (HPLC). The yield of 2-hydroxy-3-naphthoic acid amide to the starting material, 2-hydroxy-3-naphthoic acid chloride, was found to be 77 mole %.

Example 3

[Acid Chlorination Reaction]

The acid chlorination reaction was carried out in the same manner as Example 1 except that 24.6 g (0.1 mole) of 2-hydroxy-3-methoxycarbonyl-6-naphthoic acid was used instead of 23.1 g (0.1 mole) of 2-acetoxy 6-naphthoic acid and 123 g of tetrahydrofuran was used. 26.4 g (0.1 mole) of 2-hydroxy-3-methoxycarbonyl-6-naphthoic acid chloride was obtained.

[Amidation Reaction]

The amidation reaction was carried out in the same manner as Example 1 except that 2-hydroxy-3-methoxycarbonyl-6-naphthoic acid chloride obtained by the acid chlorination reaction was dissolved in 54 g of tetrahydrofuran.

The resulting reaction mixture was subjected to high performance liquid chromatography (HPLC). The yield of 2-hydroxy-3-methoxycarbonyl-6-naphthoic acid amide to the starting material, 2-hydroxy-3-methoxycarbonyl-6-naphthoic acid chloride, was found to be 72 mole %.

Example 4

[Acid Chlorination Reaction]

The acid chlorination reaction was carried out in the same manner as Example 1 except that 28.8 g (0.1 mole) of 2-hydroxy-6-n-butoxycarbonyl-3-naphthoic acid was used instead of 23.1 g (0.1 mole) of 2-acetoxy-6-naphthoic acid, 288 g of tetrahydrofuran was used and 500 ml—glass container was employed. 30.6 g (0.1 mole) of 2-hydroxy-6-n-butoxycarbonyl-3-naphthoic acid chloride was obtained.

[Amidation Reaction]

The amidation reaction was carried out in the same manner as Example 1 except that 2-hydroxy-6-n-butoxycarbonyl-3-naphthoic acid chloride obtained by the acid chlorination reaction was dissolved in 54 g of tetrahydrofuran.

The resulting reaction mixture was subjected to high performance liquid chromatography (HPLC). The yield of 2-hydroxy-6-n-butoxycarbonyl-3-naphthoic acid amide to the starting material, 2-hydroxy-6-n-butoxycarbonyl-3-naphthoic acid chloride, was found to be 88 mole %.

Example 5

According to the same manner as the acid chlorination reaction of Example 1, tetrahydrofuran and thionyl chloride were distilled out from the reaction mixture to give 2-acetoxy 6-naphthoic acid chloride as residue of evaporation. To this residue, 185 g of tetrahydrofuran was added and the mixture was heated to 40° C. and allowed to give a homogeneous solution.

To the resulting solution of 2-acetoxy-6-naphthoic acid chloride, 15.4 g (0.2 mole) of powdery ammonium acetate was added by portions at 20° C. and the amidation reaction was conducted at this temperature for 4 hours.

The resulting reaction mixture was subjected to high performance liquid chromatography (HPLC). The yield of 2-acetoxy-6-naphthoic acid amide to the starting material, 2-acetoxy-6-naphthoic acid chloride, was found to be 77 mole %.

Example 6

The acid chlorination reaction was carried out in the same manner as Example 5 except that diethylene glycol diethylether was used to dissolve the acid chloride instead of tetrahydrofuran.

The amidation reaction was carried out in the same manner as Example 5 except that diethylene glycol diethylether was used as solvent instead of tetrahydrofuran.

The resulting reaction mixture was subjected to high performance liquid chromatography (HPLC). The yield of 2-acetoxy-6-naphthoic acid amide to the starting material, 2-acetoxy-6-naphthoic acid chloride, was found to be 70 mole %.

Comparative Examples 1 to 3

The amidation reaction was carried out in the same manner as Example 5 except that ammonium salts shown in Table 1 were used instead of ammonium acetate.

The resulting reaction mixtures were subjected to high performance liquid chromatography (HPLC). The yields of 2-acetoxy-6-naphthoic acid amide to the starting material, 2-acetoxy-6-naphthoic acid chloride, were shown in Table 1.

TABLE 1

|  | Ammonium salt | Amount of ammonium salt | Yield of amide compound |
|---|---|---|---|
| Example 5 | ammonium acetate | 15.4 g | 77 mole % |
| Comparative Example 1 | ammonium formate | 12.6 g | 3.7 mole % |
| Comparative Example 2 | ammonium adipate | 18.0 g | 7.5 mole % |
| Comparative Example 3 | (+)-ammonium tartrate | 18.4 g | 0 mole % |

Comparative Examples 4 and 5

The acid chlorination reaction was carried out in the same manner as Example 5 except that solvents shown in Table 2 were used to dissolve the acid chloride instead of tetrahydrofuran.

The amidation reaction was carried out in the same manner as Example 5 except that solvents shown in Table 2 were used instead of tetrahydrofuran.

The resulting reaction mixtures were subjected to high performance liquid chromatography (HPLC). The yields of 2-acetoxy-6-naphthoic acid amide to the starting material, 2-acetoxy-6-naphthoic acid chloride, were shown in Table 2.

TABLE 2

|  | Solvent | Yield of amide compound |
|---|---|---|
| Example 5 | tetrahydrofuran | 77 mole % |
| Example 6 | diethylene glycol dimethylether | 70 mole % |
| Comparative Example 4 | xylene | 11 mole % |
| Comparative Example 5 | ethyl acetate | 21 mole % |

What is claimed is:

1. A method for producing a naphthalenecarboxylic acid amide compound represented by formula [1] comprising, reacting a naphthalenecarboxylic acid halide compound represented by formula [2] with ammonium acetate in a solvent having an ether bond:

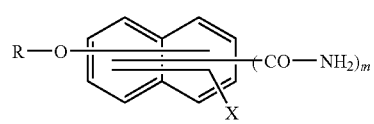

[1]

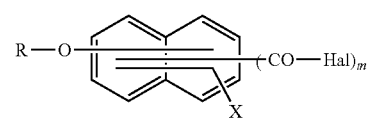

[2]

wherein, Hal is chlorine or bromine;

m is an integer of 1 or 2;

R is selected from the group consisting of hydrogen, an optionally branched saturated alkyl having 1-20 carbon atoms, an aralkyl having 7-12 carbon atoms, an optionally branched saturated alkanoyl having 2-20 carbon atoms and benzoyl group;

X is selected from the group consisting of hydrogen, cyano, a group represented by formulae [3], [4] and [5]:

—(CO—NH)$n$—Y$_1$  [3]

—CO—O—Y$_2$  [4]

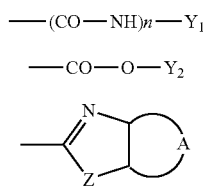 [5]

provided that when m is 2, X is hydrogen;
n is an integer of 1 or 2;
Y$_1$ is selected from the group consisting of hydrogen, an optionally branched and optionally unsaturated aliphatic group having 1-20 carbon atoms, an optionally substituted aromatic group and an optionally substituted heterocyclic group having conjugated double bonds;
Y$_2$ is an optionally branched and optionally unsaturated aliphatic group having 1-20 carbon atoms;
Z is —O—, —S— or —NH—; and
A is selected from the group consisting of an optionally substituted aromatic group and an optionally substituted heterocyclic group having conjugated double bonds.

2. The method according to claim 1, wherein the amount of ammonium acetate is 0.8-10 mole per 1 mole of halogenocarbonyl group in the naphthalenecarboxylic acid halide compound represented by formula [2].

3. The method according to claim 1, wherein Hal in formula [2] is chlorine.

4. The method according to claim 1, wherein said naphthalenecarboxylic acid halide compound is a compound represented by formula [6], [7] or [8]:

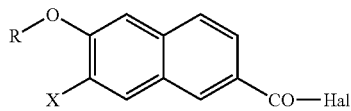 [6]

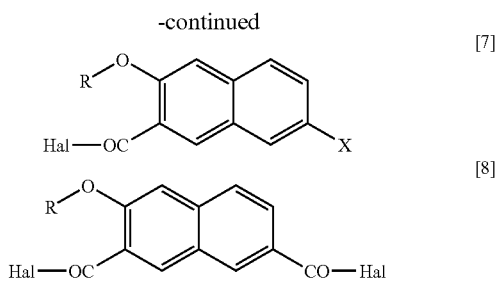

wherein, Hal, R and X in formulae [6], [7] and [8] are the same as defined in formulae [1] and [2].

5. The method according to claim 1, wherein, said naphthalenecarboxylic acid halide compound is selected from the group consisting of 2-hydroxy-3-naphthoic acid chloride, 2-hydroxy-6-naphthoic acid chloride, 2-hydroxynaphthalene-3,6-dicarboxylic acid dichloride, 2-acetoxy-3-naphthoic acid chloride, 2-acetoxy-6-naphthoic acid chloride, 2-acetoxynaphthalene-3,6-dicarboxylic acid dichloride and a mixture thereof.

6. The method according to claim 1, wherein said solvent having an ether bond is selected from the group consisting of tetrahydrofuran, 1,4-dioxane, trioxane, furan, 2-methylfuran, dimethylether, diethylether, di-n-propylether, diisopropylether, di-n-butylether, anisole, phenetol, o-methoxytoluene, m-methoxytoluene, p-methoxytoluene, ethylene glycol dimethylether, ethylene glycol diethylether, ethylene glycol dibutylether, diethylene glycol dimethylether, diethylene glycol diethylether, diethylene glycol dibutylether and a mixture thereof.

7. The method according to claim 6, wherein said solvent having an ether bond is tetrahydrofuran.

8. The method according to claim 1, comprising:
providing a mixture of the solvent having an ether bond and ammonium acetate, and
adding the naphthalenecarboxylic acid halide compound represented by formula [2] to said mixture.

* * * * *